United States Patent [19]

Jurd et al.

[11] 4,029,818

[45] June 14, 1977

[54] PROCESS FOR INHIBITING THE DETERIORATION OF WOOD DUE TO MARINE BORING ORGANISMS VIA THE USE OF DIBUTYLBENZYLPHENOL

[75] Inventors: Leonard Jurd, Berkeley, Calif.; John Dale Bultman, Washington, D.C.

[73] Assignee: The United States of America as represented by the Secretary of Agriculture, Washington, D.C.

[22] Filed: Apr. 9, 1976

[21] Appl. No.: 675,104

[52] U.S. Cl. ............................ 424/346; 21/7; 21/58

[51] Int. Cl.$^2$ ............... A61L 13/00; B27K 3/38

[58] Field of Search ............ 21/7, 58; 427/440; 260/619 R; 424/346, 331

[56] References Cited

UNITED STATES PATENTS

| 3,524,003 | 8/1970 | Reinert et al. | 424/346 |
| 3,775,541 | 11/1973 | Jurd et al. | 424/346 |

*Primary Examiner*—Morris O. Wolk
*Assistant Examiner*—Bradley Garris
*Attorney, Agent, or Firm*—M. Howard Silverstein; David G. McConnell

[57] ABSTRACT

Substances, particularly wood, which are normally subject to deterioration due to marine borers are preserved by applying to the substance a dibutylbenzylphenol.

4 Claims, No Drawings

PROCESS FOR INHIBITING THE DETERIORATION OF WOOD DUE TO MARINE BORING ORGANISMS VIA THE USE OF DIBUTYLBENZYLPHENOL

BACKGROUND OF THE INVENTION

This invention relates to the preservation of substances which are normally subject to deterioration due to marine boring organisms. The objects of the invention include the provision of novel processes and compositions for such preservation. Further objects of the invention will be evident from the following description wherein parts and percentages are by weight unless otherwise specified. Temperatures are given in degrees Centigrade. The symbol $\phi$ is used to designate the phenyl radical.

Many substances, particularly wood, are used in a marine environment, i.e., they are immersed in water for extended periods of time. One problem is that these substances are susceptible to attack and subsequent deterioration and destruction by marine boring organisms found in most bodies of water. Heretofore, such substances have been treated with whole creosote or a mixture of coal tar and cresote to preserve them. While this treatment prevents attack by marine borers for a period of time, even creosoted timbers are destroyed in a few years. Apparently, the constituents within creosote, which are toxic to marine borers, are leached from impregnated timbers and pilings into the surrounding water over a period of time. Consequently, the treated timbers eventually lose their resistance and become susceptible to damage by borer species from which they were originally protected. Repair and replacement is costly, running into many millions of dollars each year. In addition, the toxic components which are extracted into the water contribute to pollution of the environment. The future of creosote as a protectant is uncertain, not only because of its polluting tendencies, but also because it contains carcinogenic materials which are also leached out by the water.

Other preservative treatments are known but they are either not persistent or are undesirable for environmental reasons.

SUMMARY OF THE INVENTION

The invention described herein provides a means for obviating the above problems. In accordance with the invention, wood susceptible to deterioration due to marine borers can be preserved indefinitely by applying certain agents thereto prior to immersion in water.

The agents in question have the structure

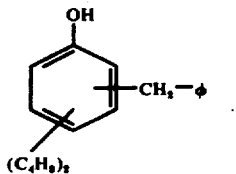

The compounds of the invention are especially useful because they are active against many types of marine borers, particularly against teredine marine borers, i.e., molluscan borers of the family, Teredinidae. The instant compounds have the advantage of being extremely insoluble in water; thus, they are not leached from the wood treated therewith. Further, because the compounds of the invention are persistent, pollution of water in which they are immersed is prevented.

DETAILED DESCRIPTION OF THE INVENTION

In preventing attack and deterioration of wood by marine borers, the specific action of the instant agents is not known. The compounds of the invention may act as marine borer larvicides, or they may act as repelling agents that deter attack by marine borers, or they may preserve the wood from attack by marine boring organisms by some other mechanism. It should be emphasized that it is not meant to limit the invention to any particular manner in which the compounds of the invention attain the desired result. We have demonstrated conclusively that the instant agents do preserve wood from attack and deterioration by marine borers.

Examples of particular compounds within the scope of the invention are given below by way of illustration and not limitation:

3,4-di-t-butyl-2-benzylphenol
3,5-di-t-butyl-2-benzylphenol
3,6-di-t-butyl-2-benzylphenol
4,5-di-t-butyl-2-benzylphenol
4,6di-t-butyl-2-benzylphenol
5,6-di-t-butyl-2-benzylphenol
3,4-di-iso-butyl-2-benzylphenol
3,5-di-iso-butyl-2-benzylphenol
3,6-di-iso-butyl-2-benzylphenol
4,5-di-iso-butyl-2-benzylphenol
4,6-di-iso-butyl-2-benzylphenol
5,6-di-iso-butyl-2-benzylphenol
3,4-di-n-butyl-2-benzylphenol
3,5-di-n-butyl-2-benzylphenol
3,6-di-n-butyl-2-benzylphenol
4,5-di-n-butyl-2-benzylphenol
4,6-di-n-butyl-2-benzylphenol
5,6-di-n-butyl-2-benzylphenol
2,3-di-t-butyl-4-benzylphenol
2,5-di-t-butyl-4-benzylphenol
2,6-di-t-butyl-4-benzylphenol
3,5-di-t-butyl-4-benzylphenol
3,6-di-t-butyl-4-benzylphenol
5,6-di-t-butyl-4-benzylphenol
2,3-di-iso-butyl-4-benzylphenol
2,5-di-iso-butyl-4-benzylphenol
2,6-di-iso-butyl-4-benzylphenol
3,5-di-iso-butyl-4-benzylphenol
3,6-di-iso-butyl-4-benzylphenol
5,6-di-iso-butyl-4-benzylphenol
2,3-di-n-butyl-4-benzylphenol
2,5-di-n-butyl-4-benzylphenol
2,6-di-n-butyl-4-benzylphenol
3,5-di-n-butyl-4-benzylphenol
3,6-di-n-butyl-4-benzylphenol
5,6-di-n-butyl-4-benzylphenol The invention encompasses not only the use of the above-described agents individually but also mixtures thereof.

In protecting substances in accordance with the invention any of the aforesaid agents or mixtures thereof are applied to the substance, using an amount of the agent which will protect the substance from deterioration, i.e., decomposition and destruction due to marine borers, when immersed in water. Possibly, this amount may be related to the amount necessary either to kill or repel the marine borers or their larvae.

For best results the wood to be protected is impregnated with any of the aforesaid agents or mixtures thereof. A solution of an agent of the invention in a suitable organic solvent is prepared and the wood is immersed therein, whereby the agent of the invention is absorbed within the wood fibers. Organic solvents which may be used to form solutions with the agents of the invention include, but are not limited to, acetone, ethyl ether, ethanol, benzene, xylene, etc.

Impregnation of the wood may be accomplished by employing any conventional wood-treating technique or facility. For example, a Bethel full-cell, vacuum/pressure technique affords an efficient means of impregnating wood with any of the above-mentioned agents.

The invention is of wide versatility and can be used for the preservation of all kinds of substances which are normally subject to deterioration due to marine borer larvae. Typical examples of such substances are listed below by way of illustration and not limitation and include softwoods and hardwoods such as cedar, ash, fir, basswood or linden, beech, birch, butternut, cottonwood or poplar, dogwood, elm, gum tree or sweet gum, hemlock, hickory, chestnut, locust, maple, oak, pine, sassafras, spruce, sycamore or buttonwood, tulip, tupelo or sour gum, walnut, redwood, larches, cypress, alder, mahogany, cherry, and the like.

As mentioned earlier, the compounds of the invention are effective in preserving substances, particularly wood, which are normally subject to deterioration due to marine bores. The agents are particularly effective against teredine marine borers, including *Lyrodus pedicellatus*, *Teredo navalis*, *T. Bartschi*, *Bankia gouldi*, *B. zetecki*, and the like.

It is within the compass of the invention to employ the instant agents with other wood preservatives. Thus, a compound of the invention or mixtures of such compounds may be incorporated with other agents which preserve wood against microorganisms, other marine organisms, etc. The resulting mixture would then be applied to the wood to be protected.

The compounds of the invention may be synthesized by known procedures. The following is a typical synthetic plan: a dibutylphenol is condensed with benzyl chloride in the presence of zinc chloride and chloroform to yield a dibutylbenzylphenol.

Some of the compounds of the invention are known compounds, disclosed by Green in U.S. Pat. No. 3,193,526. It should be emphasized, however, that Green does not disclose nor suggest that these compounds are useful as anti-marine borer agents.

DESCRIPTION OF THE PREFERRED EMBODIMENT

An acetone solution containing 3.5% of 4,6-di-t-butyl-2-benzylphenol (prepared in accordance with the procedure described by Green in U.S. Pat. No. 3,193,526) was prepared and used to treat white pin sapwood discs (¼ × 2 inch diameter). The discs were dried prior to treatment by solvent extraction according to known procedures. Impregnation of the pine discs was accomplished, using a modified Bethel full-cell treating process. The device used to treat the wood comprised a pressure/vacuum chamber and an externally connected reservoir to contain the impregnating solution. Nitrogen was applied under pressure to force the solution into the wood. Routinely, the vacuum and pressure cycles were maintained for one hour, the latter at 100 psig of the gas. At the conclusion of the treatment, each pre-weighed disc was wiped of excess solvent and weighed again to determine the amount of solution absorbed by the wood. Tests indicated that the solvent and solute were uniformly distributed throughout the wood. Excess solvent was removed by placing the discs in a vacuum dessicator at 40° for one-hour intervals until the wood no longer lost weight.

Twelve treated discs were exposed to natural borer populations in the Bay of Panama at Naos Island, Canal Zone, for a period of 6 months.

As a control discs treated with acetone only (12) and untreated discs (12) were exposed at the same time, for the same period, and in the same location as the above-mentioned discs.

After exposure, the discs were removed from the water and oven-dried to a constant weight. X-ray techniques were used to determine the extent of teredine damage. By combining a visual examination of the X-ray prints and a count of the number of boring animals present, the specimen was rated according to the following scale: 0 = no apparent damage, 1 = light damage, 2 = moderate damage, and 3 = heavy damage. The results are summarized in the table below. The damage rating is an average of the rating given to the twelve discs tested for each group.

| Agent | Amount of agent (%) | Damage |
|---|---|---|
| 4,6-di-t-butyl-2-benzylphenol | 3.5 | 0 |
| Acetone | — | 3 |
| None | — | 3 |

It should be noted that the sample discs were exposed for a period of only six months. However, since the size of the discs (¼ × 2 inch diameter) is extremely small in comparison to the expansiveness of the testing site, the six-month exposure is considered quite severe.

Having thus described our invention, we claim:

1. A process for inhibiting deterioration of wood due to marine boring organisms, which comprises applying to the wood a compound of the structure

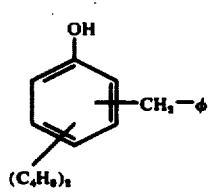

in an amount sufficient to inhibit deterioration due to marine boring organisms.

2. The process of claim 1 wherein the compound is 4,6-di-t-butyl-2-benzylphenol.

3. The process of claim 1 wherein the deterioration is due to marine borer larvae and the compound is applied in a larvicidal amount.

4. The process of claim 1 wherein the compound is applied in an amount sufficient to repel the marine boring organisms.